(12) United States Patent
Mayer

(10) Patent No.: US 6,210,624 B1
(45) Date of Patent: Apr. 3, 2001

(54) METHOD OF FORMING A RESEAL ELEMENT FOR A NEEDLELESS INJECTION SITE

(75) Inventor: Bruno Franz P. Mayer, Orange, CA (US)

(73) Assignee: Critical Device Corporation, Brea, CA (US)

( * ) Notice: Subject to any disclaimer, the term of this patent is extended or adjusted under 35 U.S.C. 154(b) by 0 days.

(21) Appl. No.: 09/137,581

(22) Filed: Aug. 21, 1998

Related U.S. Application Data

(63) Continuation-in-part of application No. 08/966,337, filed on Nov. 7, 1997, which is a continuation-in-part of application No. 08/735,217, filed on Oct. 22, 1996, now Pat. No. 5,836,923, which is a continuation-in-part of application No. 08/699,848, filed on Aug. 20, 1996, now Pat. No. 5,820,601, which is a continuation-in-part of application No. 08/493,744, filed on Jun. 22, 1995, now Pat. No. 5,616,130, which is a continuation-in-part of application No. 08/401,854, filed on Mar. 10, 1995, now Pat. No. 5,616,129, which is a continuation-in-part of application No. 08/262,994, filed on Jun. 20, 1994, now Pat. No. 5,470,319.

(51) Int. Cl.$^7$ .................................................. B29C 45/44
(52) U.S. Cl. ...................... 264/571; 264/318; 264/328.1; 264/334; 264/335; 425/577; 425/DIG. 58
(58) Field of Search .............................. 264/328.1, 334, 264/335, 318, 571, 102; 604/167; 425/577, 556, DIG. 58

(56) References Cited

U.S. PATENT DOCUMENTS

| | | |
|---|---|---|
| 3,183,292 * | 5/1965 | Dvoracek . |
| 3,977,555 | 8/1976 | Larson .................................. 215/247 |
| 4,063,460 | 12/1977 | Svensson ............................ 73/425.6 |
| 4,134,512 | 1/1979 | Nugent ................................ 215/247 |
| 4,155,698 * | 5/1979 | Aichinger . |

(List continued on next page.)

FOREIGN PATENT DOCUMENTS

| | | |
|---|---|---|
| 2001732 | 4/1990 | (CA) . |
| 3105437A1 | 10/1982 | (DE) . |
| 0309771A1 | 4/1989 | (EP) . |
| 0544581A1 | 11/1991 | (EP) . |
| 93/05838 | 4/1993 | (WO) . |
| 93/05839 | 4/1993 | (WO) . |
| 93/11828 | 6/1993 | (WO) . |
| 9600107 | 6/1994 | (WO) . |
| 97/21464 | 6/1997 | (WO) . |

OTHER PUBLICATIONS

"STAT–LINK", Universal Connector With Valve, Safe Tech Medical Products, Inc., 2 pages.

Primary Examiner—Jan H. Silbaugh
Assistant Examiner—Mark Eashoo

(57) ABSTRACT

A method of forming a reseal element through the use of a mold assembly including first and second mold plates, a shell core, a center pin, a center core, and a mold cavity having a shape corresponding to that of the reseal element and collectively defined by the first and second mold plates, the shell and center cores, and the center pin. The method comprises the initial step of injecting a quantity of a moldable material into the mold cavity to form the reseal element. Air is then infused between the shell core and the center pin into the mold cavity to dislodge the reseal element from the shell core and the center pin. Thereafter, the center core is retracted from the reseal element to define a gap therebetween, with the second plate then being retracted from over the reseal element to expose the same. The first plate is then advanced toward the second plate to remove the reseal element from upon the shell core and the center pin.

13 Claims, 3 Drawing Sheets

U.S. PATENT DOCUMENTS

| | | | |
|---|---|---|---|
| 4,246,899 | 1/1981 | Loseff | 128/276 |
| 4,301,936 | 11/1981 | Percarpio | 215/247 |
| 4,338,764 | 7/1982 | Percarpio | 53/432 |
| 4,655,752 | 4/1987 | Honkanen et al. | 604/256 |
| 4,822,270 * | 4/1989 | Bonissone et al. . | |
| 4,838,855 | 6/1989 | Lynn | 604/49 |
| 4,874,377 | 10/1989 | Newgard et al. | 604/167 |
| 4,956,143 * | 9/1990 | McFarlane . | |
| 5,064,416 | 11/1991 | Newgard et al. | 604/167 |
| 5,100,394 | 3/1992 | Dudar et al. | 604/283 |
| 5,122,123 | 6/1992 | Vaillancourt | 604/192 |
| 5,122,129 | 6/1992 | Olson et al. | 604/905 |
| 5,135,489 | 8/1992 | Jepson et al. | 604/48 |
| 5,154,703 | 10/1992 | Bonaldo | 604/244 |
| 5,158,554 | 10/1992 | Jepson et al. | 604/283 |
| 5,171,234 | 12/1992 | Jepson et al. | 604/283 |
| 5,188,620 | 2/1993 | Jepson et al. | 604/283 |
| 5,201,725 | 4/1993 | Kling | 604/284 |
| 5,203,775 | 4/1993 | Frank et al. | 604/256 |
| 5,207,661 | 5/1993 | Repschlager | 604/317 |
| 5,215,538 | 6/1993 | Larkin | 604/249 |
| 5,234,413 | 8/1993 | Wonder et al. | 604/248 |
| 5,242,425 | 9/1993 | White et al. | 604/256 |
| 5,242,432 | 9/1993 | Defrank | 604/284 |
| 5,250,033 | 10/1993 | Evans et al. | 604/160 |
| 5,269,771 | 12/1993 | Thomas et al. | 604/213 |
| 5,273,533 | 12/1993 | Bonaldo | 604/83 |
| 5,286,453 | 2/1994 | Pope | 422/100 |
| 5,324,256 | 6/1994 | Lynn et al. | 604/49 |
| 5,336,192 | 8/1994 | Palestrant | 604/167 |
| 5,360,012 | 11/1994 | Ebara et al. | 128/764 |
| 5,360,413 | 11/1994 | Leason et al. | 604/249 |
| 5,380,306 | 1/1995 | Brinon | 604/244 |
| 5,389,227 * | 2/1995 | Matyi et al. . | |
| 5,401,245 | 3/1995 | Haining | 604/86 |
| 5,439,451 | 8/1995 | Collinson et al. | 604/247 |
| 5,470,319 | 11/1995 | Mayer | 604/167 |
| 5,474,544 | 12/1995 | Lynn | 604/283 |
| 5,487,728 | 1/1996 | Vaillancourt | 604/86 |
| 5,490,966 * | 2/1996 | Peterson et al. . | |
| 5,501,426 | 3/1996 | Atkinson et al. | 251/149.1 |
| 5,509,912 | 4/1996 | Vaillancourt et al. | 604/283 |
| 5,514,116 | 5/1996 | Vaillancourt et al. | 604/283 |
| 5,520,665 | 5/1996 | Fleetwood | 604/283 |
| 5,520,666 | 5/1996 | Choudhury et al. | 604/283 |
| 5,549,566 | 8/1996 | Elias et al. | 604/167 |
| 5,549,577 | 8/1996 | Siegel et al. | 604/256 |
| 5,552,098 * | 9/1996 | Kudo et al. . | |
| 5,578,059 | 11/1996 | Patzer | 604/249 |
| 5,616,129 | 4/1997 | Mayer | 604/167 |
| 5,616,130 | 4/1997 | Mayer | 604/167 |
| 5,620,434 | 4/1997 | Brony | 604/406 |
| 5,669,891 | 9/1997 | Vaillancourt | 604/283 |
| 5,685,866 | 11/1997 | Lopez | 604/249 |
| 5,688,254 | 11/1997 | Lopez et al. | 604/283 |
| 5,690,612 | 11/1997 | Lopez et al. | 604/93 |
| 5,694,686 | 12/1997 | Lopez | 29/890.126 |
| 5,695,466 | 12/1997 | Lopez et al. | 604/93 |
| 5,699,821 | 12/1997 | Paradis | 137/1 |
| 5,700,248 | 12/1997 | Lopez | 604/249 |
| 5,788,675 * | 8/1998 | Mayer . | |
| 5,824,256 * | 10/1998 | Ballester . | |
| 5,971,965 * | 10/1999 | Mayer . | |

\* cited by examiner

Fig. 1
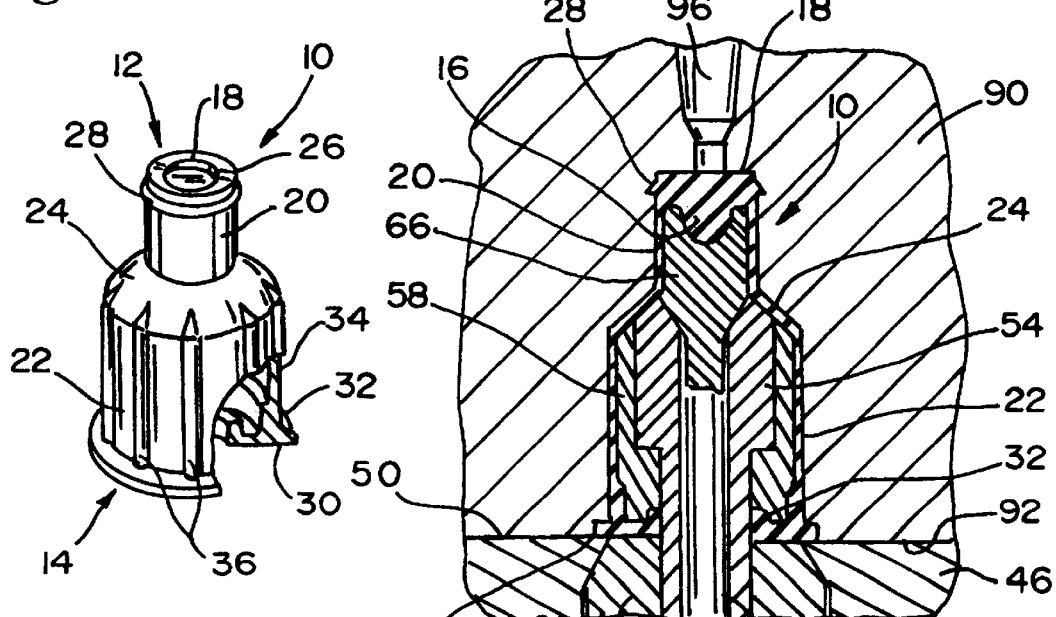
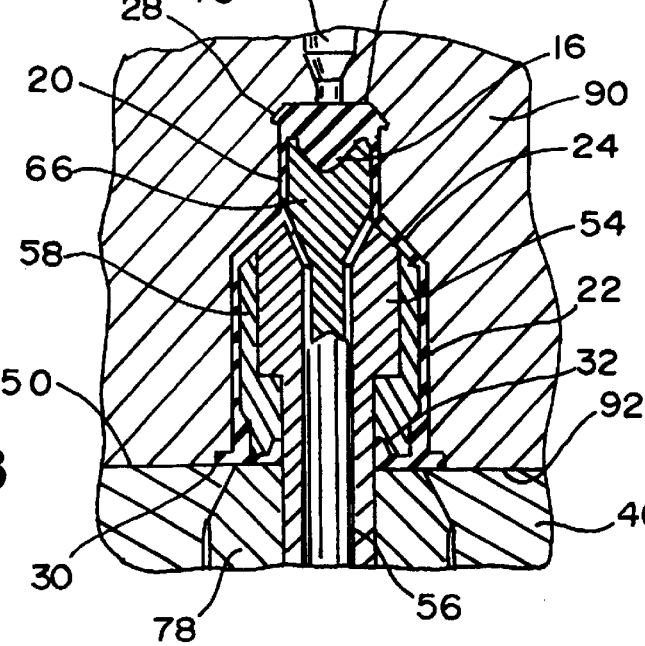
Fig. 2
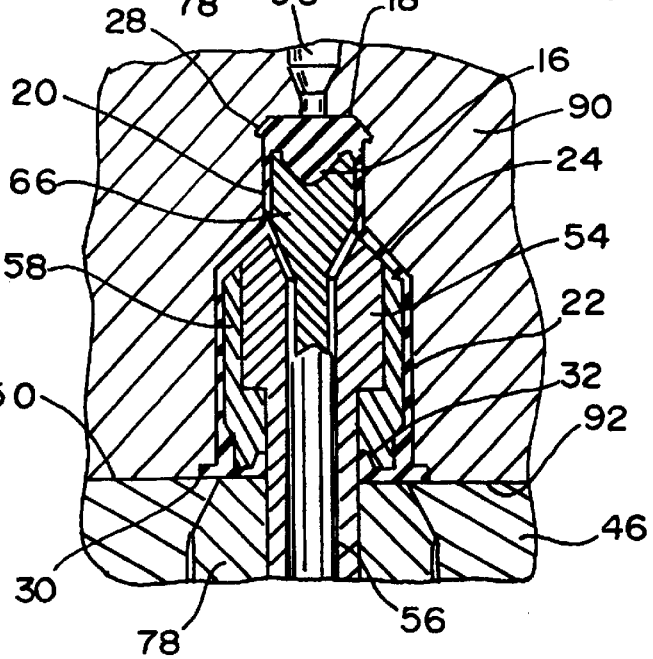
Fig. 3

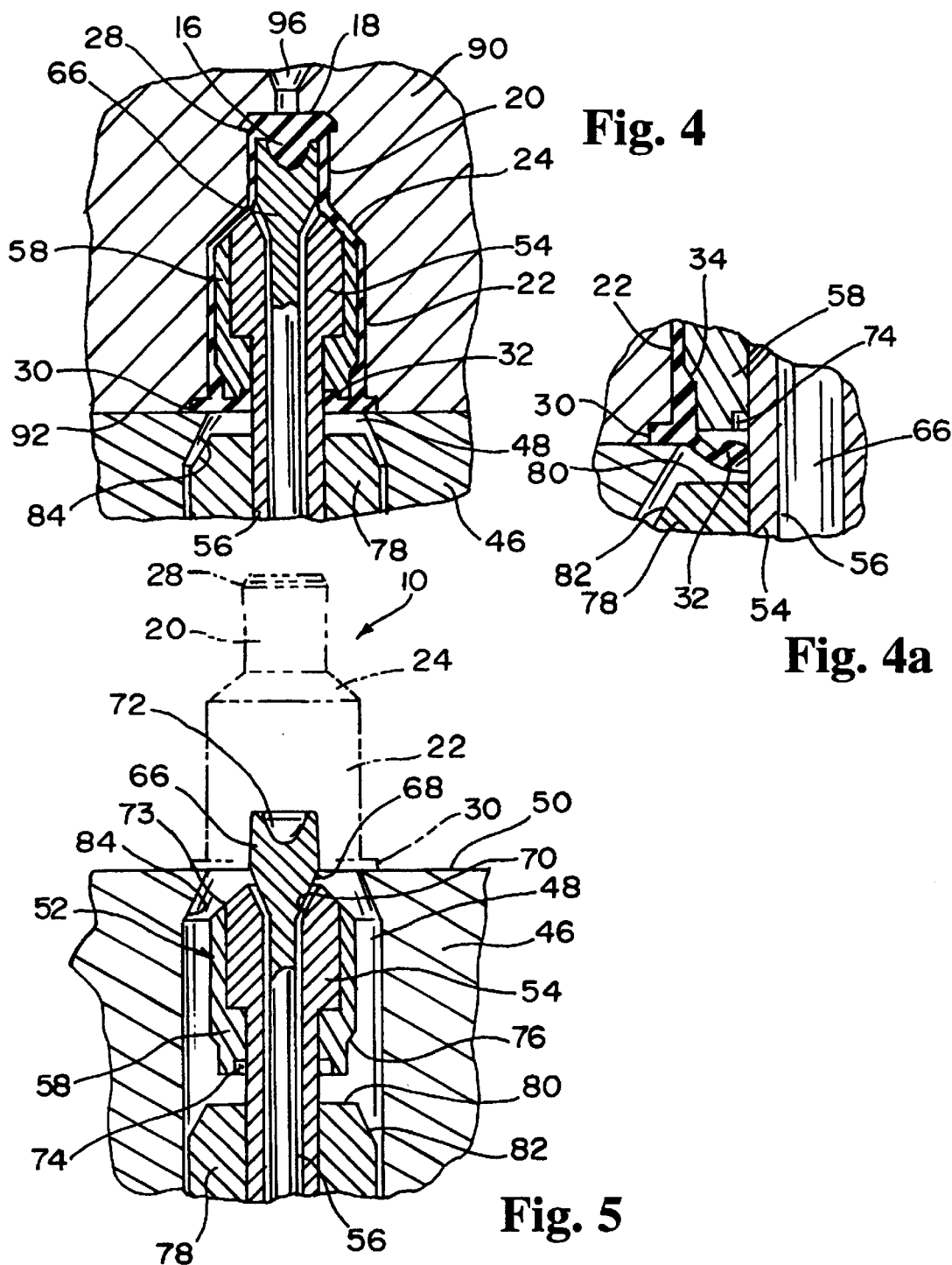

METHOD OF FORMING A RESEAL ELEMENT FOR A NEEDLELESS INJECTION SITE

RELATED APPLICATIONS

The present application is a continuation-in-part of U.S. application Ser. No. 08/966,337 entitled NEEDLELESS INJECTION SITE filed Nov. 7, 1997, which is a continuation-in-part of U.S. application Ser. No. 08/735,217 entitled NEEDLELESS INJECTION SITE WITH FIXED FLOW RATE filed Oct. 22, 1996, now U.S. Pat. No. 5,836,923 which is a continuation-in-part of U.S. application Ser. No. 08/699,848 entitled NEEDLELESS INJECTION SITE filed Aug. 20, 1996, now U.S. Pat. No. 5,820,601 which is a continuation-in-part of U.S. Ser. No. 08/493,744 filed Jun. 22, 1995 entitled NEEDLELESS INJECTION SITE now U.S. Pat. No. 5,616,130 issued Apr. 1, 1997, which is a continuation-in-part of U.S. Ser. No. 08/401,854 filed Mar. 10, 1995 entitled NEEDLELESS INJECTION SITE now U.S. Pat. No. 5,616,129 issued Apr. 1, 1997, which is a continuation-in-part of U.S. Ser. No. 08/262,994 filed Jun. 20, 1994 entitled NEEDLELESS INJECTION SITE now U.S. Pat. No. 5,470,319 issued Nov. 28, 1995, the disclosures of which are expressly incorporated herein by reference.

FIELD OF THE INVENTION

The present invention relates generally to the medical arts, and more particularly to a method of forming a reseal element for use in a needleless injection site having particular utility in relation to intravenous infusion applications.

BACKGROUND OF THE INVENTION

It is common medical practice to intravenously infuse various fluids or medicaments into a blood vessel of a patient (e.g., a vein or artery). Such infusion is typically accomplished by the insertion of a hollow introducer needle into a target blood vessel. The introducer needle is fluidly connected to one end of an elongate, flexible tube or fluid line, the opposite end of which is fluidly connected to a solution bag. The solution bag itself is typically suspended above the patient so as to allow gravity to facilitate the flow of fluid downwardly through the fluid line and into the patient's blood vessel via the introducer needle which remains operatively positioned therewithin. The fluid tube and solution bag are connected to each other via a metering apparatus which controls the infusion rate of fluid from the bag into the tube.

In many intravenous infusion assemblies, an injection site is fluidly coupled within the tubing intermediate the introducer needle and the solution bag. The injection site typically has a Y-shaped configuration and comprises a tubular main body portion having a tubular side arm portion in fluid communication therewith. The distal end of the side arm portion is fluidly connected to the solution bag via an upper segment of the tubing, with the bottom end of the main body portion being fluidly connected to the introducer needle via a lower segment of the tubing. The top end of the main body portion is itself covered by a diaphragm which is typically fabricated from rubber or a similar resilient material.

The inclusion of the injection site within the tubing allows various medications to be selectively infused into the blood vessel of the patient by the addition thereof to the solution flowing from the solution bag into the blood vessel via the upper tubing segment, injection site, lower tubing segment and introducer needle. This supplemental infusion is typically accomplished through the utilization of a conventional syringe, the needle of which pierces and is extended through the diaphragm disposed on the top end of the main body portion of the injection site. Subsequent to the expulsion of the medication from within the syringe and into the flowing solution, the needle is retracted out of the main body portion of the injection site, with the aperture created in the diaphragm due to the passage of the needle therethrough being substantially closed upon such retraction due to the resiliency of the diaphragm. As will be recognized, the incorporation of the injection site within the tubing allows various medications to be intravenously administered to the patient through the existing infusion site within the blood vessel, thus eliminating the need to subject the patient to additional needle sticks.

Though providing certain benefits to the patient, the injection sites constructed in accordance with the prior art possess certain deficiencies which detract from their overall utility. As previously explained, the use of such injection sites typically requires that the needle of the conventional syringe be extended through (i.e., puncture) the diaphragm attached to the top end of the main body portion of the injection site. However, the necessity of having to utilize a syringe with a needle to facilitate the introduction of the medication into the solution flow is undesirable due to the risk of inadvertent needle sticks.

In recognition of this deficiency, there has also been developed in the prior art needleless injection sites which incorporate a diaphragm adapted to assume open and closed configurations without having a needle inserted thereinto. Though these needleless injection sites eliminate the necessity of having to puncture the diaphragm with a needle, they also possess certain deficiencies which detract from their overall utility. Foremost of these deficiencies is the difficulty associated with disinfecting the injection site, and in particular the diaphragm thereof, subsequent to medication being infused thereinto. In this respect, after each use of the injection site the diaphragm must be cleaned, with such cleaning typically being accomplished through the application of alcohol or a similar disinfecting agent thereto. However, due to the configuration of the diaphragm, complete and effective disinfection thereof is often difficult to achieve, thus increasing the risk of the inadvertent introduction of contaminates into the solution stream upon subsequent uses of the injection site.

In an effort to overcome the deficiencies associated with the prior art injection sites, Applicant developed the needleless injection sites disclosed in the previously identified issued patents and co-pending applications which are the parent cases of the present application. The present needleless injection site constitutes an improvement over those disclosed in the parent cases. In this respect, the present injection site is provided with design features which are adapted to prevent the inadvertent obstruction of the fluid flow path, and to increase the level of positive flow within the fluid flow path such that the withdrawal of a needled or non-needled introducer from within the injection site does not cause a vacuum to be pulled within a tubular fluid line connected thereto.

In an effort to overcome the deficiencies associated with the prior art injection sites, Applicant developed the needleless injection sites disclosed in the previously identified issued patents and co-pending applications which are the parent cases of the present application. In the parent application immediately preceding the present application, Applicant's needleless injection site is provided with design features which are adapted to prevent the inadvertent obstruction of the fluid flow path, and to increase the level of positive flow within the fluid flow path such that the withdrawal of a needled or non-needled introducer from within the injection site does not cause a vacuum to be pulled within a tubular fluid line connected thereto. These design features are largely embodied in the reseal member of the needleless injection site. The present invention provides a unique methodology for forming the reseal member, and in particular the body element thereof.

SUMMARY OF THE INVENTION

In accordance with the present invention, there is provided a novel and unique method for forming a reseal element of a reseal member used in a needleless injection site. Further in accordance with the present invention, there is provided a mold assembly for carrying out such method. The mold assembly comprises a movable first or bottom plate which defines a generally planar top surface and includes a core opening extending therethrough. In addition to the first plate, the mold assembly comprises a shell core which extends through the core opening of the first plate and protrudes from the top surface of the first plate. The shell core itself defines a flow passage which extends therethrough.

Extending through the flow passage of the shell core and protruding therefrom is a center pin of the mold assembly. The center pin is operable to selectively block the flow passage defined by the shell core. More particularly, the center pin is movable relative to the shell core between a pin molding position whereat the flow passage is blocked by the abutment of the centering pin against the shell core and an air blow position whereat the flow passage is unblocked by the extension of the center pin from the shell core in an amount sufficient to create a gap therebetween. The first plate is selectively movable upwardly and downwardly along those portions of the shell core and the center pin protruding from the top surface thereof.

The mold assembly of the present invention further comprises a center core which also extends within the core opening of the first plate and is selectively retractable thereinto. More particularly, the center core, which defines a generally planar top end, is movable relative to the first plate between a core molding position whereat the top end is substantially flush and continuous with the top surface of the first plate, and an ejection position whereat the top end is retracted inwardly into the first plate and spaced from the top surface thereof.

In addition to the above-described components, the mold assembly of the present invention includes a second or top plate which defines a generally planar bottom surface and is selectively advanceable over those portions of the shell core and the center pin protruding from the first plate such that a mold cavity having a shape corresponding to that of the reseal element is collectively defined by the first and second plates, the shell and center cores, and the center pin. More particularly, the second plate is movable between a plate molding position whereat the bottom surface thereof is disposed immediately adjacent the top surface of the first plate, and an unloading position whereat the bottom surface is retracted away and spaced from the top surface of the first plate. As will be recognized, the first plate is movable along the shell core and the center pin toward the second plate when the second plate is in its unloading position.

In the mold assembly of the present invention, the shell core itself comprises an inner sleeve which defines the flow passage, and an outer sleeve which circumvents a portion of the inner sleeve. Additionally, a vacuum port is disposed within the first plate, with an inlet port being disposed within the second plate. Both the vacuum and inlet ports fluidly communicate with the mold cavity, with the inlet port being used to inject the moldable material into the mold cavity and the vacuum port being used to evacuate the mold cavity prior to the injection of the moldable material thereinto.

In the preferred method of the present invention, the molding process is initiated with the second plate being in its plate molding position, the center pin being in its pin molding position, and the center core being in its core molding position. When the second plate, center pin, and center core are in these particular positions, the mold cavity is collectively defined by the first and second mold plates, the shell and center cores, and the center pin. The initial step of the preferred method comprises creating a vacuum within the mold cavity via the vacuum port extending within the first plate. Thereafter, a quantity of moldable material is injected into the mold cavity via the inlet port extending within the second plate. The preferred moldable material injected into the mold cavity is silicone. After being injected into the mold cavity, the moldable material is allowed to cure for a prescribed period of time to form the reseal element.

Subsequent to the formation of the reseal element, the center pin is moved to its air blow position so as to allow for the infusion of pressurized air into the mold cavity from the flow passage of the shell core. In this respect, upon the unblocking of the flow passage accomplished by the movement of the center pin to its air blow position, pressurized air flows through the flow passage and between the shell core and the center pin, and directly impinges the reseal element. Such flow effectively dislodges the reseal element from upon the shell core and the center pin.

As the pressurized air is being infused into the mold cavity in the above-described manner, the center core of the mold assembly is moved from its core molding position to its ejection position. The gap defined between the top end of the center core and the reseal element by the movement of the center core to its ejection position allows a portion of the formed reseal element which curls underneath the shell core to be dislodged therefrom and rotated outwardly out of contact therewith by the pressurized air impinging the reseal element via the flow passage.

Subsequent to or simultaneous with the movement of the center core to its ejection position, the second plate of the mold assembly is moved to its unloading position so as to expose the formed reseal element and to create a substantial space or gap between the top surface of the first plate and the bottom surface of the second plate. After the second plate has been moved to its unloading position, the first plate is moved upwardly along those portions of the shell core and the center pin protruding therefrom so as to remove or strip the formed reseal element from upon the shell core and the center pin. The infusion of the pressurized air against the reseal element via the flow passage is continued until such time as the first plate travels upwardly beyond the shell core to the center pin.

In the mold assembly of the present invention, the shell and center cores and center pin thereof comprise a molding unit. It is contemplated that the present method may be implemented on a mold press including the first and second plates and multiple mold units disposed within the first plate in a generally circular configuration.

BRIEF DESCRIPTION OF THE DRAWINGS

These, as well as other features of the present invention, will become more apparent upon reference to the drawings wherein:

FIG. 1 is a partial cross-sectional view of a reseal element formed in accordance with the methodology of the present invention;

FIGS. 2, 3, 4, 4a and 5 are partial cross-sectional views illustrating a preferred sequence of steps employed in the methodology of the present invention for forming the reseal element shown in FIG. 1.

DETAILED DESCRIPTION OF THE PREFERRED EMBODIMENT

Figure 6:
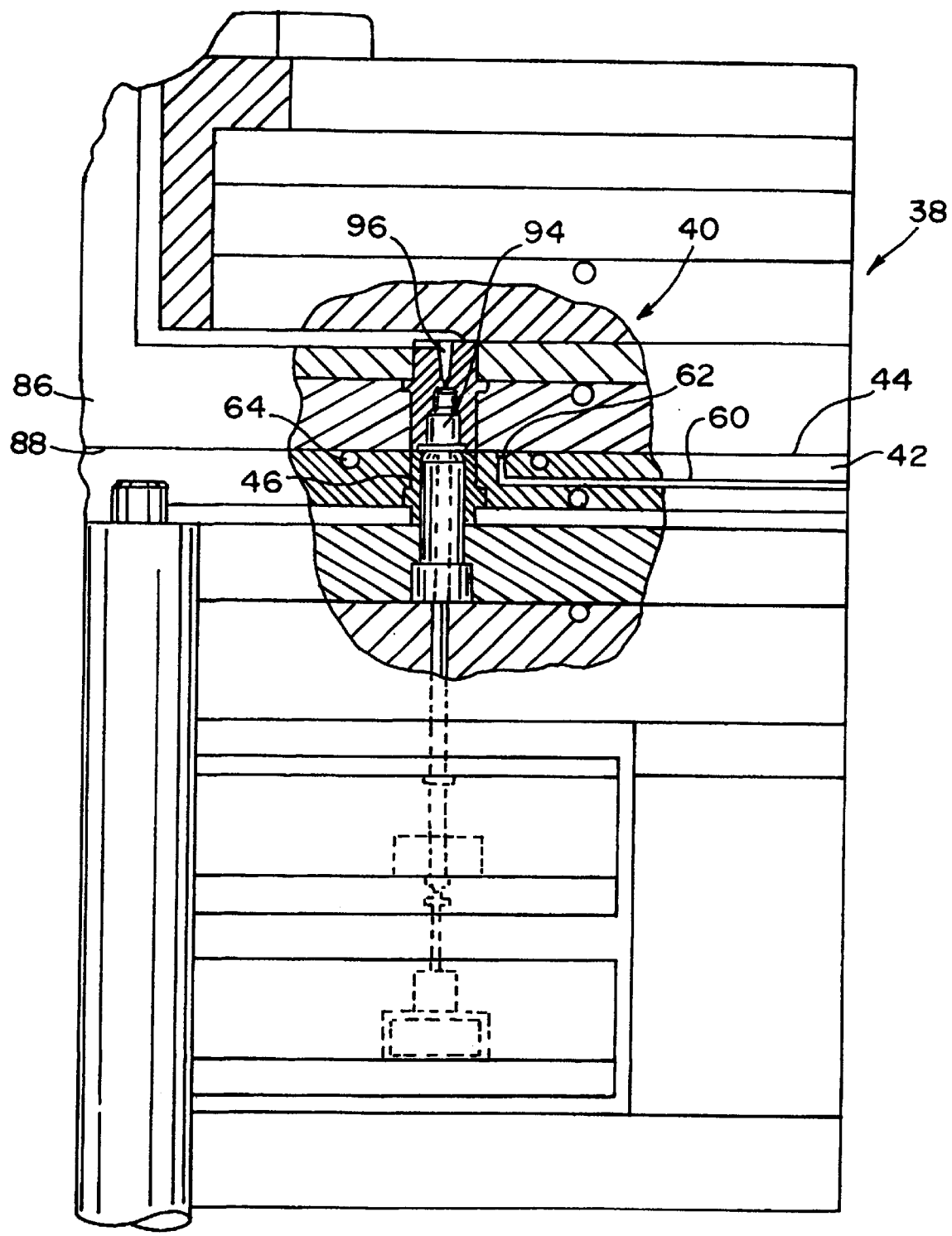
FIG. 6 is a partial cross-sectional view of a mold press used to carry out the sequence of steps shown in FIGS. 2–5.

Referring now to the drawings wherein the showings are for purposes of illustrating a preferred embodiment of the present invention only, and not for purposes of limiting the same, FIG. 1 perspectively illustrates a reseal element 10 formed using the molding apparatus and associated forming methodology depicted in FIGS. 2–6. The reseal element 10 is substantially similar, both structurally and functionally, to the body of the reseal member described in the immediately preceding parent application. In this respect, the reseal element 10 includes a proximal end 12 and a distal end 14, with the proximal end 12 defining an inner surface 16 and an outer surface 18. The proximal end 12 is defined by a generally cylindrical proximal portion 20 of the reseal element 10, which also includes a generally cylindrical distal portion 22. The proximal and distal portions 20, 22 are separated by a beveled shoulder 24 formed therebetween, and are sized such that the diameter of the distal portion 22 exceeds the diameter of the proximal portion 20.

In the reseal element 10, the inner surface 16 of the proximal end 12 has a generally semi-spherical configuration. Additionally, formed in the outer surface 18 of the proximal end 12 is a circularly configured depression 26 which is centrally positioned within the outer surface 18. Further, formed on the proximal portion 20 is a centering ring 28 which extends thereabout and has a generally wedge-shaped cross-sectional configuration.

The distal end 14 of the reseal element 10 is defined by an annular flange 30 which is formed on the distal portion 22 and extends radially inward and outward relative thereto. Formed on the inner peripheral edge of the flange 30 is an enlarged bead 32. In the reseal element 10, the distal portion 22 is not of a uniform wall thickness, but rather includes a section of increased thickness adjacent the flange 30 which is separated from the remainder of the distal portion 22 by a beveled shoulder 34. Additionally, formed on the outer surface of the distal portion 22 in equidistantly spaced relation to each other are a plurality of elongate compression ribs 36 which extend from the shoulder 24 to the flange 30.

The reseal element 10 is formed through the use of a mold press 38 shown in FIG. 6. The mold press 38 is provided with at least one mold assembly 40 which comprises a movable first or bottom plate 42. The first plate 42 defines a generally planar top surface 44 and includes a tubular first sleeve 46 disposed therein. The first sleeve 46 defines a core opening 48 which extends axially therethrough, and an annular, generally planar top end 50 which is substantially flush and continuous with the top surface 44 of the first plate 42. Since the first sleeve 46 is rigidly mounted within the first plate 42, the movement of the first plate 42 facilitates the concurrent movement of the first sleeve 46.

Extending within the first plate 42 is an elongate vacuum passage 60, one end of which terminates at an annular vacuum port 62 disposed within the top surface 44 of the first plate 42. The annular vacuum port 62 circumvents the top end 50 of the first sleeve 46. Also disposed within the top surface 44 of the first plate 42 is an annular O-ring groove 64 which accommodates an O-ring. When the O-ring is disposed within the O-ring groove 64, it protrudes slightly above the top surface 44 of the first plate 42. Importantly, the O-ring groove 64 is oriented within the top surface 44 such that it circumvents both the top end 50 of the first sleeve 46 and vacuum port 62. The use of both the vacuum port 62 and O-ring within the O-ring groove 64 will be discussed in more detail below.

In addition to the first plate 42, the mold assembly 40 comprises a shell core 52 which extends through the core opening 48 of the first sleeve 46 and protrudes upwardly from the top end 50 thereof. The shell core 52 itself comprises an elongate, tubular inner sleeve 54 which includes an enlarged upper portion and defines a flow passage 56 extending axially therethrough. In addition to the inner sleeve 54, the shell core 52 includes an outer sleeve 58 which circumvents a portion of the inner sleeve 54 adjacent the top end thereof. When the inner and outer sleeves 54, 58 are attached to each other, they collectively define an upper beveled shoulder 73 and a lower annular groove 74. Additionally, formed in the outer surface of the outer sleeve 58 is a beveled shoulder 76.

The mold assembly 40 of the present invention further comprises an elongate center pin 66 which extends axially through the flow passage 56 of the inner sleeve 54 and protrudes from the top end thereof. As seen in FIGS. 2 and 3, the upper portion of the center pin 66 is enlarged relative to the remainder thereof and defines a beveled shoulder 68 having a configuration which is complimentary to that of the beveled shoulder 70 which defines the top end of the flow passage 56. Formed within the top end of the center pin 66 is a semi-circular recess 72.

In the mold assembly 40, the center pin 66 is operable to selectively block the flow passage 56 defined by the inner sleeve 54 of the shell core 52. More particularly, as seen in FIGS. 2 and 3, the center pin 66 is movable relative to the inner sleeve 54 between a pin molding position (shown in FIG. 2) whereat the flow passage 56 is blocked by the abutment of the shoulder 68 of the center pin 66 against the complimentary shoulder 70 of the inner sleeve 54, and an air blow position (shown in FIGS. 3 and 4) whereat the flow passage 56 is unblocked by the extension of the center pin 66 from the inner sleeve 54 in an amount sufficient to create a gap between the shoulders 68, 70. Importantly, the diameter of the center pin 66 other than for the enlarged upper portion thereof is substantially less than the diameter of the flow passage 56 so as not to block the same. As will be discussed in more detail below, the first plate 42 of the mold assembly 40 is selectively movable upwardly and downwardly along those portions of the shell core 52 and the center pin 66 protruding from the top end 50 of the first sleeve 46.

The mold assembly 40 of the present invention further comprises an elongate center core 78 which also extends within the core opening 48 of the first sleeve 46. The center core 76 has a generally cylindrical configuration, and defines an annular, generally planar top end 80 which is separated from the remainder thereof by a beveled shoulder 82 formed in the outer surface of the center core 78. As best seen in FIG. 6, the inner sleeve 54 of the shell core 52 extends axially through the center core 78 and is slidable therewithin. The center core 78 of the mold assembly 40 is selectively retractable into the interior of the inner sleeve 54 in the manner shown in FIGS. 3 and 4. More particularly, the center core 78 is movable relative to the inner sleeve 54 between a core molding position (shown in FIGS. 2 and 3) whereat the top end 80 is substantially flush and continuous with the top end 50 of the first sleeve 46, and an ejection position whereat the top end 80 is retracted inwardly into the first sleeve 46 and spaced from the top end 50 thereof. The accurate location of the center core 78 to its core molding position is facilitated by the abutment of the beveled shoulder 82 thereof against a corresponding, complimentary beveled shoulder 84 defined by the inner surface of the first sleeve 46 which defines the core opening 48.

In addition to the above-described components, the mold assembly 40 of the present invention includes a movable second or top plate 86 which defines a generally planar bottom surface 88. Disposed within the second plate 86 is a second sleeve 90 which defines an annular, generally planar bottom end 92. The second sleeve 90 is rigidly mounted within the second plate 86 in a manner wherein the bottom end 92 thereof is substantially flush and continuous with the bottom surface 88 of the second plate 86. The second sleeve 90 includes a recess 94 formed therein having a shape corresponding to the outer surface contours of the reseal element 10. In addition to the recess 94, disposed within the second sleeve 90 is a inlet port 96 which fluidly communicates with the recess 94 and is used for injecting a moldable material thereinto as will be discussed in more detail below.

In the mold assembly 40, the second plate 86, and in particular the second sleeve 90, is selectively advanceable over those portions of the shell core 52 and the center pin 66 which protrude upwardly from the top end 50 of the first sleeve 46. More particularly, the second plate 86 is movable between a plate molding position whereat the bottom surface 88 thereof is disposed immediately adjacent the top surface 44 of the first plate 42, and an unloading position whereat the bottom surface 88 is retracted away and spaced from the top surface 44 of the first plate 42. When the second plate 86 is in its plate molding position, those portions of the shell core 52 and center pin 66 protruding upwardly from the inner sleeve 54 are received into the recess 94 of the second sleeve 90. Thus, when the second plate 86 is in its plate molding position, the center pin 66 is in its pin molding position, and the center core 78 is in its core molding position, a mold cavity having a shape corresponding to that of the reseal element 10 is collectively defined by the first and second plates 42, 86, shell and center cores 52, 78, and center pin 66. As will be recognized, the first plate 42 is movable upwardly along the shell core 52 and center pin 66 only after the second plate 86 has been actuated to its unloading position.

Having thus described the components of the mold assembly 40, a preferred method of forming the reseal element 10 through the use of the mold assembly 40 will now be described with particular reference to FIGS. 2–5. In the present invention, the molding process is initiated when the second plate 86 is in its plate molding position, the center pin 66 is in its pin molding position, and the center core 78 is in its core molding position. As indicated above, when the second plate 86, center pin 66, and center core 78 are in these particular positions, the mold cavity corresponding in shape to that of the reseal element 10 is collectively defined by the first and second mold plates 42, 86, the shell and center cores 52, 78, and the center pin 66.

The initial step of the preferred method comprises creating a vacuum within the mold cavity via the vacuum port 62 and vacuum passage 60 within the first plate 42. When the second plate 86 is in its plate molding position, a very narrow gap is defined between the bottom surface 88 of the second plate 86 and the top surface 44 of the first plate 42, and between the top end 50 of the first sleeve 46 and the bottom end 92 of the second sleeve 90. Due to this gap, the creation of a vacuum within the vacuum passage 60 and vacuum port 62 effectively evacuates the interior of the mold cavity. Importantly, the O-ring within the O-ring groove 64 creates a fluid-tight seal between the first and second plates 42, 86 as is needed to effectively create the vacuum within the mold cavity.

Subsequent to the mold cavity being evacuated, a quantity of moldable material is injected into the mold cavity via the inlet port 96 extending within the second sleeve 90. The preferred moldable material injected into the mold cavity is silicone, though those of ordinary skill in the art will recognize that other suitable alternative materials may be employed in the manufacture of the reseal element 10. After being injected into the mold cavity, the moldable material is allowed to cure for a prescribed period of time to form the reseal element 10.

As indicated above, the shape of the mold cavity corresponds to that of the reseal element 10. For example, the semi-circular inner surface 16 of the reseal element 10 is formed by the flow of the moldable material into the semi-circular recess 72 within the top end of the center pin 66. Additionally, the proximal portion 90 of the reseal element 10 is formed by the flow of the moldable material about the outer surface of the enlarged upper portion of the center pin 66, with the distal portion 22 being formed by the flow of the moldable material about the outer surface of the outer sleeve 58, and the shoulder 24 being formed by the flow of the moldable material over the beveled shoulder 73 collectively defined by the inner and outer sleeves 54, 58 of the shell core 52. Further, the bead 32 of the reseal element 10 is formed by the flow of moldable material into the groove 74, with the shoulder 34 being formed by the flow of moldable material against the shoulder 76 within the outer surface of the outer sleeve 58.

Subsequent to the formation of the reseal element 10 in the manner shown in FIG. 2, the center pin 66 is moved to its air blow position in the manner shown in FIG. 3 so as to allow for the infusion of pressurized air into the mold cavity from the flow passage 56 of the shell core 52. In this respect, upon the unblocking of the flow passage 56 accomplished by the movement of the center pin 66 to its air blow position, pressurized air flows through the flow passage 56 between the inner sleeve 54 and center pin 66. After flowing between the shoulders 68, 70 of the inner sleeve 54 and center pin 66, the pressurized air directly impinges the formed reseal element 10. Such flow or impingement effectively dislodges the reseal element 10 from upon the inner and outer sleeves 54, 58 of the shell core 52 and the enlarged upper portion of the center pin 66. Due to the second plate 86 being in its plate molding position, the movement of the center pin 66 to its air blow position results in a slight compression of the proximal end 12 of the formed reseal element 10 between the top end of the center pin 66 and the second sleeve 90.

As the pressurized air is being infused into the mold cavity in the above-described manner, the center core 78 of the mold assembly 40 is moved from its core molding position (shown in FIGS. 2 and 3) to its ejection position (shown in FIG. 4). The resultant gap defined between the top end 80 of the center core 78 and the flange 30 of the reseal element 10 by the movement of the center core 78 to its ejection position allows the formed flange 30 which curls underneath the outer sleeve 58 of the shell core 52 to be dislodged therefrom and rotated outwardly out of contact therewith by the pressurized air impinging the reseal element 10 in the manner shown in FIG. 4a.

Subsequent to or simultaneous with the movement of the center core 78 to its ejection position, the second plate 86 of the mold assembly 40 is moved to its unloading position so as to expose the formed reseal element 10 and to create a substantial space or gap between the top surface 44 of the first plate 42 and the bottom surface 88 of the second plate 86. After the second plate 86 has been moved to its unloading position, the first plate 42 is moved upwardly along those portions of the shell core 52 and the center pin 66 protruding therefrom so as to remove or strip the formed reseal element 10 from upon the shell core 52 and the center pin 66 in the manner shown in FIG. 5. The infusion of the pressurized air against the reseal element 10 via the unblocked flow passage 56 is preferably continued until such time as the top end 50 of the first sleeve 46 travels upwardly beyond the inner sleeve 54 of the shell core 52.

Referring to FIG. 6, the mold press 38 is provided with various components as are needed to facilitate the upward and downward movement of the first plate 42, the infusion of pressurized air into the flow passage 56 and the movement of the center pin 66 between its pin molding and air blow positions, the movement of the center core 78 between its core molding and ejection positions, the movement of the second plate 86 between its plate molding and unloading positions, the creation of a vacuum within the vacuum passage 60, and the injection of a moldable material into the inlet port 96. It is contemplated that the first and second sleeves 90, shell and center cores 52, 78 and center pin 66 may comprise a molding unit, and that the present method may be implemented on the mold press 38 which includes the first and second plates 42, 86 having multiple mold units disposed therein in a generally circular configuration so as to facilitate the simultaneous fabrication of multiple reseal elements 10.

Additional modifications and improvements of the present invention may also be apparent to those of ordinary skill in the art. Thus, the particular parts and steps described and illustrated herein are intended to represent only one embodiment of the present invention, and are not intended to serve as limitations of alternative devices and methods within the spirit and scope of the invention.

What is claimed is:

1. A method of forming a reseal element through the use of a mold assembly including first and second mold plates, a shell core, a center pin, a center core, and a mold cavity having a shape corresponding to that of the reseal element and collectively defined by the first and second mold plates, the shell and center cores, and the center pin, the method comprising the steps of:

(a) injecting a quantity of a moldable material into the mold cavity to form the reseal element;

(b) infusing air between the shell core and the center pin into the mold cavity to dislodge the reseal element from the shell core and the center pin;

(c) retracting the center core from the reseal element to define a gap therebetween;

(d) retracting the second plate from over the reseal element to expose the reseal element;

(e) advancing the first plate toward the second plate to remove the reseal element from upon the shell core and the center pin; and wherein step (a) occurs first, and steps (c) and (d) occur prior to step (e).

2. The method of claim 1 wherein step (a) comprises injecting silicone into the mold cavity.

3. The method of claim 1 wherein step (a) comprises creating a vacuum within the mold cavity prior to the injection of the moldable material thereinto.

4. The method of claim 1 wherein step (b) is continued until after the initiation of step (e).

5. A method of forming a reseal element comprising the steps of:

(a) providing a mold assembly which includes first and second mold plates, a shell core, a center pin, a center core, and a mold cavity having a shape corresponding to that of the reseal element and collectively defined by the first and second mold plates, the shell and center cores, and the center pin;

(b) injecting a quantity of a moldable material into the mold cavity to form the reseal element;

(c) infusing air between the shell core and the center pin into the mold cavity to dislodge the reseal element from the shell core and the center pin;

(d) retracting the center core from the reseal element to define a gap therebetween;

(e) retracting the second plate from over the reseal element to expose the reseal element;

(f) advancing the first plate toward the second plate to remove the reseal element from upon the shell core and the center pin; and wherein step (a) occurs first, step (b) occurs second, and steps (d) and (e) occur prior to step (f).

6. The method of claim 5 wherein step (b) comprises injecting silicone into the mold cavity.

7. The method of claim 5 wherein step (b) comprises creating a vacuum within the mold cavity prior to the injection of the moldable material thereinto.

8. The method of claim 5 wherein step (b) comprises injecting the moldable material into the mold cavity via the second plate.

9. The method of claim 5 wherein step (c) is continued until after the initiation of step (f).

10. The method of claim 5 wherein:

the shell core defines a flow passage which extends therethrough;

the center pin extends through the shell core; and step (c) comprises moving the center pin from a pin molding position whereat the flow passage is blocked by the abutment of the centering pin against the shell core to an air blow position whereat the flow passage is unblocked by the extension of the center pin from the shell core in an amount sufficient to create a gap therebetween.

11. The method of claim 5 wherein:

the first plate defines a generally planar top surface;

the center core defines a generally planar top end and extends within the first plate; and step (d) comprises moving the center core from a core molding position whereat the top end is substantially continuous with the top surface to an ejection position whereat the top end is retracted inwardly into the first plate and spaced from the top surface thereof.

12. The method of claim 11 wherein:

the second plate defines a generally planar bottom surface; and step (e) comprises moving the second plate from a plate molding position whereat the bottom surface is disposed immediately adjacent the top surface of the first plate to an unloading position whereat the bottom surface is retracted away and spaced from the top surface of the first plate.

13. The method of claim 12 wherein:

the shell core and the center pin extend through the first plate and protrude from the top surface thereof; and step (f) comprises moving the first plate along the shell core and the center pin toward the second plate when the second plate is in the unloading position.

* * * * *